United States Patent
Mrksich et al.

(10) Patent No.: US 10,782,287 B2
(45) Date of Patent: Sep. 22, 2020

(54) ENZYME COUPLED ASSAY FOR QUANTIFICATION OF PROTEIN AND PEPTIDE BINDING BY SAMDI MASS SPECTROMETRY

(71) Applicant: NORTHWESTERN UNIVERSITY, Evanston, IL (US)

(72) Inventors: Milan Mrksich, Hinsdale, IL (US); Patrick O'Kane, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 845 days.

(21) Appl. No.: 15/051,338

(22) Filed: Feb. 23, 2016

(65) Prior Publication Data

US 2016/0252501 A1 Sep. 1, 2016

Related U.S. Application Data

(60) Provisional application No. 62/119,409, filed on Feb. 23, 2015.

(51) Int. Cl.
*G01N 33/543* (2006.01)

(52) U.S. Cl.
CPC . *G01N 33/54306* (2013.01); *G01N 33/54353* (2013.01); *G01N 2333/47* (2013.01); *G01N 2333/98* (2013.01); *G01N 2560/00* (2013.01)

(58) Field of Classification Search
None
See application file for complete search history.

(56) References Cited

U.S. PATENT DOCUMENTS

| | | |
|---|---|---|
| 2010/0004137 A1 | 1/2010 | Mrksich et al. |
| 2010/0112722 A1 | 5/2010 | Mrksich et al. |
| 2012/0142547 A1 | 6/2012 | Mrksich et al. |

OTHER PUBLICATIONS

Paulmurugan et al (Molecular Imaging and Biology vol. 12 p. S1352. Abstract No. 0382) (Year: 2010).*
Seeliger et al (ACS Chem Biol 7:150-4) (Year: 2012).*
Ladbury et al (PNAS 92:3199-03) (Year: 1995).*
Ban et al., Discovery of glycosyltransferases using carbohydrate arrays and mass spectrometry. *Nat. Chem. Biol.* 8: 769-73 (2012).
Ban et al., On-chip synthesis and label-free assays of oligosaccharide arrays. *Angew. Chem. Int. Ed. Eng.* 47: 3396-9 (2008).
Bannister et al., Selective recognition of methylated lysine 9 on histone H3 by the HP1 chromo domain. *Nature*, 410: 120-4 (2001).
Buchanan et al., Structure-based design and synthesis of a novel class of Src SH2 inhibitors. *Bioorg. Med. Chem. Lett.* 9: 2353-8 (1999).
Cabrera-Pardo et al., Label-assisted mass spectrometry for the acceleration of reaction discovery and optimization. *Nat. Chem.* 5: 423-7 (2013).
Cai et al., Enzymatic synthesis and properties of uridine-5'-O-(2-thiodiphospho)-N-acetylglucosamine. *Carbohydr. Res.* 346: 1576-80 (2011).
Chung et al., Discovery and characterization of small molecule inhibitors of the BET family bromodomains. *J. Med. Chem.* 54: 3827-38 (2011).
Dekker et al., Histone acetyl transferases as emerging drug targets. *Drug Discov. Today*, 14: 942-8 (2009).
Dillmore et al., A photochemical method for patterning the immobilization of ligands and cells to self-assembled monolayers. *Langmuir*, 20: 7223-31 (2004).
Dormann et al., Dynamic regulation of effector protein binding to histone modifications: the biology of HP1 switching. *Cell Cycle*, 5: 2842-51 (2006).
Eisert et al., Tuning HP1α chromodomain selectivity for di- and trimethyllysine. *ChemBioChem*, 12: 2786-90 (2011).
Eissenberg, Structural biology of the chromodomain: form and function. *Gene*, 496: 69-78 (2012).
Fanti, HP1: a functionally multifaceted protein. *Curr. Opin. Genet. Dev.* 18: 169-74 (2008).
Feng et al., The synergy peptide PHSRN and the adhesion peptide RGD mediate cell adhesion through a common mechanism. *Biochemistry*, 43: 15811-21 (2004).
Garske et al., Combinatorial profiling of chromatin binding modules reveals multisite discrimination. *Nat. Chem. Biol.* 6: 283-90 (2010).
Gawalt et al., A substituent effects study reveals the kinetic pathway for an interfacial reaction. *J. Am. Chem. Soc.* 126: 15613-7 (2004).
Gurard-Levin et al., Combining mass spectrometry and peptide arrays to profile the specificities of histone deacetylases. *Chembiochem.* 10: 2159-61 (2009).
Gurard-Levin et al., Combining self-assembled monolayers and mass spectrometry for applications in biochips. *Annu. Rev. Anal. Chem.* (Palo Alto Calif.) 1: 767-800 (2008).
Gurard-Levin et al., High-throughput screening of small molecule libraries using SAMDI mass spectrometry. *ACS Comb. Sci.* 13: 347-50 (2011).
Gurard-Levin et al., Peptide arrays identify isoform-selective substrates for profiling endogenous lysine deacetylase activity. *ACS Chem. Biol.* 5: 863-73 (2010).
Gurard-Levin et al., The activity of HDAC8 depends on local and distal sequences of its peptide substrates. *Biochemistry*, 47: 6242-50 (2008).
Herold et al., Drug discovery toward antagonists of methyl-lysine binding proteins. *Curr. Chem. Genom.* 5: 51-61 (2011).
Herold et al., Small-molecule ligands of methyl-lysine binding proteins. *J. Med. Chem.* 54: 2504-11 (2011).

(Continued)

Primary Examiner — Christopher M Gross
(74) Attorney, Agent, or Firm — Marshall, Gerstein & Borun LLP (57) ABSTRACT

Disclosed herein are methods of using an immobilized substrate, immobilized ligand, and a fusion protein of an enzyme for the substrate and a receptor for the ligand, where the immobilized substrate can react to form an immobilized product that has a different mass than the immobilized substrate, and using this transformation to indirectly determine the binding of the receptor and the ligand. These methods can be used for high-throughput screening for possible modulators (e.g., inhibitors or activators) of the ligand-receptor interaction.

23 Claims, 4 Drawing Sheets
Specification includes a Sequence Listing.

(56) References Cited

OTHER PUBLICATIONS

Hodneland et al., Biomolecular surfaces that release ligands under electrochemical control. *J. Am. Chem. Soc.* 122: 4235-6 (2000).
Hodneland et al., Design of self-assembled monolayers that release attached groups using applied electrical potentials. *Langmuir*, 13: 6001-3 (1997).
Hodneland et al., Selective immobilization of proteins to self-assembled monolayers presenting active site-directed capture ligands. *Proc. Natl. Acad. Sci. USA*, 99: 5048-52 (2002).
Houseman et al., Carbohydrate arrays for the evaluation of protein binding and enzymatic modification. *Chem. Biol.* 9: 443-54 (2002).
Houseman et al., Maleimide-functionalized self-assembled monolayers for the preparation of peptide and carbohydrate biochips. *Langmuir*, 19: 1522-31 (2003).
Houseman et al., Model systems for studying polyvalent carbohydrate binding interactions. *Top. Curr. Chem.* 218: 1-44 (2002).
Houseman et al., Peptide chips for the quantitative evaluation of protein kinase activity. *Nat. Biotechnol.* 20: 270-4 (2002).
Houseman et al., The microenvironment of immobilized Arg-Gly-Asp peptides is an important determinant of cell adhesion. *Biomaterials*, 22: 943-55 (2001).
Houseman et al., The role of ligand density in the enzymatic glycosylation of carbohydrates presented on self-assembled monolayers of alkanethiolates on gold. *Angew. Chem. Int. Ed.* 38: 782-5 (1999).
Houseman et al., Towards quantitative assays with peptide chips: a surface engineering approach. *Trends Biotechnol.* 20: 279-81 (2002).
Hublitz et al., Mechanisms of transcriptional repression by histone lysine methylation. *Int. J. Dev. Biol.* 53: 335-54 (2009).
James et al., Subcellular curvature at the perimeter of micropatterned cells influences lamellipodial distribution and cell polarity. *Cell Motil. Cytoskeleton.* 65: 841-52 (2008).
Kato et al., 7. Using model substrates to study the influence of affinity on cell adhesion. Abstracts, Division of Biological Chemistry, 222nd National Meeting of the American Chemical Society, Aug. 26-29, 2001, *Biochemistry*, 40: 8607-64 (2001).
Kato et al., Rewiring cell adhesion. *J. Am. Chem. Soc.* 126: 6504-5 (2004).
Kaustov et al., Recognition and specificity determinants of the human cbx chromodomains. *J. Biol. Chem.* 286: 521-9 (2011).
Kim et al., Profiling the selectivity of DNA ligases in an array format with mass spectrometry. *Nucleic Acids Res.* 38: e2 (2010).
Kraskouskaya et al., Progress towards the development of SH2 domain inhibitors. *Chem. Soc. Rev.* 42: 3337-70 (2013).
Kwon et al., Dependence of the rate of an interfacial Diels-Alder reaction on the steric environment of the immobilized dienophile: an example of enthalpy-entropy compensation. *J. Am. Chem. Soc.* 124: 806-12 (2002).
Lane et al., Histone deacetylase inhibitors in cancer therapy. *J. Clin. Oncol.* 27: 5459-68 (2009).
Lee et al., Protein nanoarrays generated by dip-pen nanolithography. *Science*, 295: 1702-5 (2002).
Li et al., Catalytic asymmetric dihydroxylation by gold colloids functionalized with self-assembled monolayers. *Langmuir*, 15: 4957-9 (1999).
Li et al., Rapid evaluation and screening of interfacial reactions on self-assembled monolayers. *Langmuir*, 23: 11826-35 (2007).
Li et al., Rate enhancement of an interfacial biochemical reaction through localization of substrate and enzyme by an adaptor domain. *J. Phys. Chem. B*. 114: 15113-8 (2010).
Li et al., Steady-state of an enzymatic reaction is dependent on the density of reactant. *Langmuir*, 294-8 (2013).
Liao et al., A spatially propagating biochemical reaction. *Angew. Chem. Int. Ed. Engl.* 50: 706-9 (2011).
Liao et al., An adaptor domain-mediated autocatalytic interfacial kinase reaction. *Chemistry*, 15: (2009). 12303-09.
Liu et al., Systematic identification of methyllysine-driven interactions for histone and nonhistone targets. *J. Proteome Res.* 9: 5827-36 (2010).
Luk et al., 233. Stereochemical control of cell adhesion on self-assembled monolayers presenting organized saccharides: Potential effects of template water structure. Abstracts, Division of Biological Chemistry, 226th National Meetings of the American Chemical Society, Sep. 7-11, 2003. *Biochemistry*, 42: 8594-652 (2003).
Luk et al., Self-assembled monolayers of alkanethiolates presenting mannitol groups are inert to protein adsorption and cell attachment. *Langmuir*, 16: 9604-8 (2000).
Marin et al., Functional assays of membrane-bound proteins with SAMDI-TOF mass spectrometry. *Angew. Chem. Int. Ed. Engl.* 46: 8796-8 (2007).
Min et al., A method for connecting solution-phase enzyme activity assays with immobilized format analysis by mass spectrometry. *Anal. Chem.* 76: 3923-9 (2004).
Min et al., Peptide arrays: towards routine implementation. *Curr. Opin. Chem. Biol.* 8: 554-8 (2004).
Min et al., Profiling kinase activities by using a peptide chip and mass spectrometry. *Angew. Chem. Int. Ed. Engl.* 43: 5973-7 (2004).
Montavon et al., Three-component reaction discovery enabled by mass spectrometry of self-assembled monolayers. *Nat. Chem.* 4: 45-51 (2012).
Mrksich et al., Using self-assembled monolayers that present oligo(ethylene glycol) groups to control the interactions of proteins with surfaces. *ACS Symp. Ser.* 680: 361-73 (1997).
Mrksich et al., Using self-assembled monolayers to understand the interactions of man-made surfaces with proteins and cells. *Annu. Rev. Biophys. Biomol. Struct.* 25: 55-78 (1996).
Mrksich, A surface chemistry approach to studying cell adhesion. *Chem. Soc. Rev.* 29: 267-73 (2000).
Mrksich, Dynamic substrates for cell biology. *MRS Bull.* 30: 180-4 (2005).
Mrksich, Mass spectrometry of self-assembled monolayers: a new tool for molecular surface science. *ACS Nano*, 2: 7-18 (2008).
Mrksich, Tailored substrates for studies of attached cell culture. *Cell Mol. Life Sci.* 54: 653-62 (1998).
Mrksich, Using self-assembled monolayers to understand the biomaterials interface. *Curr. Opin. Colloid Int. Sci.* 2: 83-8 (1997).
Mrksich, What can surface chemistry do for cell biology? *Curr. Opin. Chem. Biol.* 6: 794-7 (2002).
Murphy et al., Substrates for cell adhesion prepared via active site-directed immobilization of a protein domain. *Langmuir*, 20: 1026-30 (2004).
Mwakwari et al., Non-peptide macrocyclic histone deacetylase inhibitors derived from tricyclic ketolide skeleton. *J. Med. Chem.* 53: 6100-11 (2010).
Patil et al., 3-Hydroxypyridin-2-thione as novel zinc binding group for selective histone deacetylase inhibition. *J. Med. Chem.* 56: 3492-506 (2013).
Patrie et al., Self-assembled monolayers for MALDI-TOF mass spectrometry for immunoassays of human protein antigens. *Anal. Chem.* 79: 5878-87 (2007).
Prats Alfonso et al., Cancer prognostics by direct detection of p53-antibodies on gold surfaces by impedance measurements. *Small*, 8: 2106-15 (2012).
Sanchez et al., The role of human bromodomains in chromatin biology and gene transcription. *Curr. Opin. Drug Discov. Devel.* 12: 659-65 (2009).
Sigal et al., Using surface plasmon resonance spectroscopy to measure the association of detergents with self-assembled monolayers of hexadecanethiolate on gold. *Langmuir*, 13: 2749-55 (1997).
Sperl et al., Natural product inhibitors of protein-protein interactions mediated by Src-family SH2 domains. *Bioorg. Med. Chem. Lett.* 19: 3305-9 (2009).
Su et al., Using MALDI-TOF mass spectrometry to characterize interfacial reactions on self-assembled monolayers. *Langmuir*, 19: 4867-70 (2003).
Su et al., Using mass spectrometry to characterize self-assembled monolayers presenting peptides, proteins, and carbohydrates. *Angew. Chem. Int. Ed. Engl.* 41: 4715-8 (2002).
Sudol, From Src Homology domains to other signaling modules: proposal of the 'protein recognition code'. *Oncogene*, 17: 1469-74 (1998).

(56) References Cited

OTHER PUBLICATIONS

Tsubery et al., Biochemical assays of immobilized oligonucleotides with mass spectrometry. *Langmuir*, 24: 5433-8 (2008).
Volkmer et al., Synthetic peptide arrays for investigating protein interaction domains. *FEBS Lett.* 586: 2780-6 (2012).
Whitcomb et al., Polycomb Group proteins: an evolutionary perspective. *Trends Genet.* 23: 494-502 (2007).
Yeo et al., Electroactive monolayer substrates that selectively release adherent cells. *Chembiochem.* 2: 590-3 (2001).
Yeo et al., Electroactive substrates that reveal aldehyde groups for bio-immobilization. *Adv Mater.* 16: 1352-6 (2004).
Yeo et al., Label-free detection of protein-protein interactions on biochips. *Angew. Chem. Int. Ed. Engl.* 44: 5480-3 (2005).
Yeo et al., Self-assembled monolayers that transduce enzymatic activities to electrical signals. *Angew. Chem. Int. Ed. Engl.* 42: 3121-4 (2003).
Yonzon et al., A comparative analysis of localized and propagating surface plasmon resonance sensors: the binding of concanavalin a to a monosaccharide functionalized self-assembled monolayer. *J. Am. Chem. Soc.* 126: 12669-76 (2004).
Yousaf et al., *Biochemistry*, 39: 1580-1580 (2000).
Yousaf et al., Diels-Alder Reaction for the selective immobilization of protein to electroactive self-assembled monolayers. *J. Am. Chem. Soc.* 121: 4286-7 (1999).
Yousaf et al., The kinetic order of an interfacial diels-Alder Reaction depends on the environment of the immobilized dienophile. *Angew. Chem. Int. Ed. Engl.* 39: 1943-6 (2000).
Yousaf et al., Turning on cell migration with electroactive substrates. *Angew. Chem. Int. Ed. Engl.* 40: 1093-6 (2001).
Yousaf et al., Using electroactive substrates to pattern the attachment of two different cell populations. *Proc. Natl. Acad. Sci. USA*, 98: 5992-6 (2001).
Houseman et al., Environment of Arg-Gly-Asp ligands influences the adhesion of fibroblasts to self-assembled monolayers. *Cell Attachment to the Extracellular Matrix*, p. 430a, Abstract 2494 (1998).
Houseman et al., Model substrates for the dynamic control of cell behavior. *Extracellular Matrix Cell Bahavior*, p. 45a, Abstract 232 (2000).
Houseman et al., Using self-assembled monolayers that present Arg-Gly-Asp peptide ligands to study adhesion of fibroblasts. *Extracellular Matrix-Cell Interaction*, 11: p. A1095, Abstract 1395 (1997).
International Search Report and Written Opinion from International Application No. PCT/US2016/019163 dated Aug. 8, 2016.

\* cited by examiner

ENZYME COUPLED ASSAY FOR QUANTIFICATION OF PROTEIN AND PEPTIDE BINDING BY SAMDI MASS SPECTROMETRY

CROSS-REFERENCE TO RELATED APPLICATIONS

This application claims the priority benefit under 35 U.S.C. § 119(e) of U.S. Provisional Application No. 62/119,409, filed Feb. 23, 2015, the disclosure of which is incorporated herein by reference in its entirety.

STATEMENT OF GOVERNMENT INTEREST

This invention was made with government support under grant number N66001-11-1-4179 awarded by the Defense Advanced Research Projects Agency (DARPA). The government has certain rights in the invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 2013-090_Seqlisting.txt; Size: 1,488 bytes, created: Feb. 23, 2016.

FIELD OF THE INVENTION

The present disclosure is directed to high throughput, label-free methods of profiling binding interactions.

BACKGROUND OF THE INVENTION

Protein-protein interactions are highly prevalent and play integral roles in many biological systems. These interactions can localize proteins or enzymes to specific cellular targets and are also involved in the formation of protein complexes. The technologies for measuring these interactions, however, are limited. Available assays with high throughput are limited to qualitative comparisons and require detectable labels. More quantitative options lack throughput and often require prohibitively large sample sizes. Additionally, their ubiquity in cellular systems makes protein interactions attractive drug targets, but the lack of assays to assess these interactions makes identifying therapeutics tedious. Most assays for measuring these interactions seek to quantify protein in the bound versus unbound state, and so the signal is intrinsically limited by the strength of the interaction.

Protein-ligand interactions are important in virtually all signaling pathways and therefore offer new opportunities as targets for drug discovery. Yet, the current assays that measure protein-ligand interactions do not have the throughput to be useful in the high throughput screening campaigns that are important at the start of the discovery process. Many of these techniques are also ill-suited to measuring weak protein-ligand interactions.

The development of high throughput assays has allowed a thousand-to-million-fold increase in the number of assays that can be run on a sample and has led to the discovery of small molecule inhibitors of enzyme activity, of new protein activities, and of modes of regulation of cellular pathways. Yet, many of the assays are directed at measuring enzyme activities and high affinity protein-ligand interactions. The development of high throughput assays that can measure weak protein-ligand interactions remains particularly challenging and currently there is a lack of assays that can be used to screen weak interactions. The development of high throughput assays that can measure weak ligand-receptor interactions will enable drug discovery on new classes of epigenetic targets, those not possessing enzymatic activity, and in that sense can have a transforming impact in cancer biology and therapy.

SUMMARY OF THE INVENTION

The present disclosure provides methods of using an immobilized substrate, immobilized ligand, and a fusion protein of an enzyme for the substrate and a receptor for the ligand, where the immobilized substrate can react to form an immobilized product that has a different mass than the immobilized substrate, and using this transformation to indirectly determine the binding of the receptor and the ligand.

These methods provide high throughput screening assays to identify modulators of receptor-ligand interactions. In one aspect, the disclosure provides an array-based assay for screening low affinity protein-protein or protein-peptide interactions. The methods of the disclosure are not limited by the amount of bound versus unbound substrate, but rather by a covalent "history" of interactions that had occurred. Thus, the methods are particularly significant for measuring complexes of lower affinity that are not amenable to, for example, pull-down formats.

In one aspect, the present disclosure provides an assay that utilizes an enzyme-catalyzed reaction to report on the binding of an adaptor domain to an immobilized ligand. The assay utilizes a surface that presents two peptides; one peptide is a substrate for an enzyme and the other peptide is a ligand for a chromodomain. A fusion protein of the chromodomain and the enzyme is applied to the surface. In one embodiment, the substrate is selected such that its rate of deacetylation is slow, but when the chromodomain is bound to its ligand, the localization of the enzyme to the surface leads to an accelerated rate for the enzyme-catalyzed reaction. In this way, the deacetylation reaction proceeds when the receptor-ligand interaction is operating, and provides an integrated record of the receptor-ligand interaction.

Accordingly, in another aspect, the disclosure provides a method comprising (a) contacting an immobilized substrate and an immobilized ligand with a fusion protein under conditions to transform the immobilized substrate to an immobilized product, wherein the immobilized product has a mass different from the immobilized substrate; the fusion protein comprises (1) an enzyme capable of transforming the substrate to the product and (2) a receptor, and the immobilized substrate for the enzyme and the immobilized ligand for the receptor are each bound to a self-assembled monolayer (SAM) on a surface; (b) subjecting the substrate and product to mass spectrometry to produce a mass spectrum having a product signal and a substrate signal; and (c) detecting binding of the receptor and the ligand by correlating a signal intensity of the product to a signal intensity of the substrate to determine the extent of product formation and thereby detecting the binding of the receptor and the ligand, wherein the total density of the ligand and the substrate on the surface is less than or equal to about 10%.

In some embodiments, the total density of the ligand and the substrate on the surface is from about 3% to about 7%. In various embodiments, the total density of the ligand and the substrate on the surface is from about 5% to about 6%.

In some cases, the total density of the ligand and the substrate on the surface is at least about 0.1%.

In various embodiments of the methods of the disclosure, the extent of product formation in the presence of the fusion protein is greater than extent of product formation in the presence of the enzyme not fused to the receptor. In related embodiments, the extent of product formation in the presence of the fusion protein is at least 2 times greater, at least 5 times greater, at least 10 times greater, at least 20 times greater, at least 30 times greater, or at least 50 times greater than extent of product formation in the presence of the enzyme not fused to the receptor.

In some embodiments, at least one of the substrate and ligand is bound to the surface via a linker. The linker, in some embodiments, has a structure of formula I:

(formula I)

wherein L is the substrate or ligand.

In some embodiments, L is attached to the pyrrolindinone of formula (I) via a thiol bond. In further embodiments, the linker is attached to the SAM via an ethylene glycol moiety.

In some embodiments, the SAM is attached to the surface via a thiol bond. The surface, in various embodiments, comprises gold. In various cases, the surface comprises silver, while in yet another embodiment, the surface comprises copper.

In various embodiments, at least one of the substrate and the ligand comprises a peptide. In some embodiments, the peptide is bound to the SAM via a cysteine residue. In further embodiments, at least one of the substrate and the ligand comprises a protein.

In various embodiments, the enzyme is a deacetylase, acetyltransferase, esterase, phosphorylase/kinase, phosphatase, protease, methylase, demethylase, or a DNA or RNA modifying enzyme. In some embodiments, the esterase is cutinase or acetylcholine esterase. In further embodiments, the protease is TEV.

In some embodiments, the deacetylase is KDAC8. In further embodiments, the esterase is cutinase or acetylcholine esterase. In additional embodiments, the protease is TEV.

In various embodiments, the substrate comprises an acylated peptide and the product comprises a deacylated peptide. In further embodiments, the substrate comprises a deacylated peptide and the product comprises an acylated peptide.

In various embodiments, the substrate comprises a phosphorylated peptide and the product comprises a dephosphorylated peptide. In some embodiments, the substrate comprises a dephosphorylated peptide and the product comprises a phosphorylated peptide.

In various embodiments, the substrate comprises a methylated peptide and the product comprises a demethylated peptide. In further embodiments, the substrate comprises a demethylated peptide and the product comprises a methylated peptide.

In some embodiments, the receptor is a chromodomain, a bromodomain, a PDZ domain, a Src homology 2 (SH2) domain SH2 domain, or a PDZ domain. In various embodiments, the chromodomain is a HP1 chromodomain, or a Pc chromodomain.

In various embodiments, the ligand is a peptide and comprises a methylated lysine residue.

In some embodiments, the substrate density on the surface is greater than the ligand density on the surface.

In some embodiments, the ligand has a dissociation constant ($K_D$) of about 10 μM to about 100 μM. In various embodiments, the ligand has a dissociation constant ($K_D$) of about 100 μM to about 10 μM. In various embodiments, the ligand $K_D$ is less than 10 μM.

In various embodiments, methods of the disclosure further comprise contacting the immobilized substrate and the immobilized ligand with the fusion protein in the presence of one or more potential modulators of the receptor-ligand binding; subjecting the substrate and product to mass spectrometry to produce a mass spectrum having a product signal and a substrate signal; and detecting binding of the receptor and the ligand by correlating a signal intensity of the product to a signal intensity of the substrate to determine the extent of product formation and thereby detecting the binding of the receptor and the ligand in the presence of the one or more potential modulators. In some embodiments, the modulator is an inhibitor of the receptor-ligand binding. In various embodiments, the modulator is an activator of the receptor-ligand binding.

In various embodiments, methods of the disclosure further comprise admixing a matrix to the substrate and product prior to subjecting the substrate and product to mass spectrometry.

DETAILED DESCRIPTION OF THE INVENTION

The present disclosure describes methods for measuring binding interactions, such as protein-protein and protein-peptide interactions. The methods are based on the SAMDI mass spectrometry technique (U.S. Patent Application Publication Number 2010/0112722, incorporated herein by reference in its entirety) and use matrix-assisted laser desorption-ionization mass spectrometry to analyze self-assembled monolayers.

Self-Assembled Monolayer Substrates. The present disclosure contemplates the use of self-assembled monolayers as substrates for assay applications (Mrksich et al., Annu Rev Biophys Biomol Struct 25: 55-78 (1996); Hodneland et al., Langmuir 13: 6001-6003 (1997); Houseman et al., FASEB J 11: A1095-A1095 (1997); Mrksich, Curr Opin Colloid In 2: 83-88 (1997); Mrksich et al., Acs Sym Ser 680: 361-373 (1997); Houseman et al., Mol Biol Cell 9: 430a-430a (1998); Mrksich, Cell Mol Life Sci 54: 653-662 (1998); Houseman et al., Angew Chem Int Ed 38: 782-785 (1999); Li et al., Langmuir 15: 4957-4959 (1999); Yousaf et al., J Am Chem Soc 121: 4286-4287 (1999); Houseman et al., Mol Biol Cell 11: 45a-45a (2000); Luk et al., Langmuir 16: 9604-9608. (2000); Mrksich, Chem Soc Rev 29: 267-273 (2000); Yousaf et al., Angew Chem Int Ed Engl 39: 1943-1946 (2000); Yousaf et al., Biochemistry 39: 1580-1580 (2000); Houseman et al., Biomaterials 22: 943-955 (2001); Kato et al., Biochemistry 40: 8608-8608 (2001); Yeo et al., Chembiochem 2: 590-593 (2001); Yousaf et al., Proc Natl Acad Sci USA 98: 5992-5996. (2001); Yousaf et al., Angew Chem Int Ed Engl 40: 1093-1096 (2001); Hodneland et al., Proc Natl Acad Sci USA 99: 5048-5052 (2002); Houseman et al., Nat Biotechnol 20: 270-274 (2002); Houseman et al., Top Curr Chem 218: 1-44 (2002); Houseman et al., Trends Biotechnol 20: 279-281 (2002); Houseman et al., Chem Biol 9: 443-454 (2002); Kwon et al., J Am Chem Soc 124: 806-812 (2002); Lee et al., Science 295: 1702-1705 (2002); Mrksich, Curr Opin Chem Biol 6: 794-797 (2002); Houseman et al., Langmuir 19: 1522-1531 (2003); Luk et al., Biochemistry 42: 8647-8647 (2003); Yeo et al., Angew Chem Int Ed Engl 42: 3121-3124 (2003); Dillmore et al., Langmuir 20: 7223-7231 (2004); Feng et al., Biochemistry 43: 15811-15821 (2004); Kato et al., J Am Chem Soc 126: 6504-6505 (2004); Min et al., Curr Opin Chem Biol 8: 554-558 (2004); Murphy et al., Langmuir 20: 1026-1030 (2004); Yeo et al., Adv Mater 16: 1352-1356 (2004); Yonzon et al., J Am Chem Soc 126: 12669-12676 (2004); Mrksich, MRS Bull 30: 180-184 (2005); James et al., Cell Motil Cytoskeleton 65: 841-852 (2008)). Previous work utilized a monolayer that presented a peptide against a background of tri(ethylene glycol) groups (Houseman et al., Nat Biotechnol 20: 270-274 (2002)). The peptide was a substrate for Src kinase and the glycol groups prevented non-specific adsorption of protein to the monolayer. Treatment of the monolayer with enzyme and ATP resulted in phosphorylation of the peptide, which was detected by measuring radioactivity from a $^{32}P$ label or by using an anti-phosphotyrosine antibody with detection by fluorescence scanning or surface plasmon resonance spectroscopy. This example showed that the use of monolayers gave solid-phase assay with exceptional performance. It further indicated that blocking procedures were unnecessary; the signal was 80-fold above background; and that enzyme constants and inhibitor dissociation constants could be measured quantitatively. The monolayers offer the benefits that immobilized ligands are presented in a homogeneous environment and the density of the immobilized ligands can be controlled and made uniform across the entire array (Gawalt et al., J Am Chem Soc 126: 15613-7 (2004)). The monolayers are also compatible with a range of immobilization chemistries (Montavon et al., Nat Chem 4: 45-51 (2012); Ban et al., Nat Chem Biol 8: 769-773 (2012); Li et al., Langmuir 23, 11826-11835 (2007)). In these respects, the monolayers are more effective as substrates in assay applications than is the nitrocellulose material (or even the common use of glass). A significant additional benefit of the monolayer substrates is that they can be analyzed by matrix-assisted laser desorption-ionization mass spectrometry (i.e., SAMDI mass spectrometry) and therefore provide a route to label-free assays of biochemical activities (Su et al., Langmuir 19: 4867-4870 (2003)).

SAMDI Mass Spectrometry.

SAMDI mass spectrometry can be used to detect the mass of a substrate or product. In this way, when the monolayer is treated with an enzyme that modifies the immobilized substrate, the resulting mass change of the immobilized product can be detected with mass spectrometry. The assay is applicable to a broad range of post-translational activities, can be performed in high throughput using plates having a number of distinct reaction zones (e.g., 1536) offering a throughput of about 50,000 assays per day, and is quantitative with Z-factors greater than 0.8. The assay can also be used to screen small molecule libraries to identify inhibitors or activators of enzymes.

Figure 1:
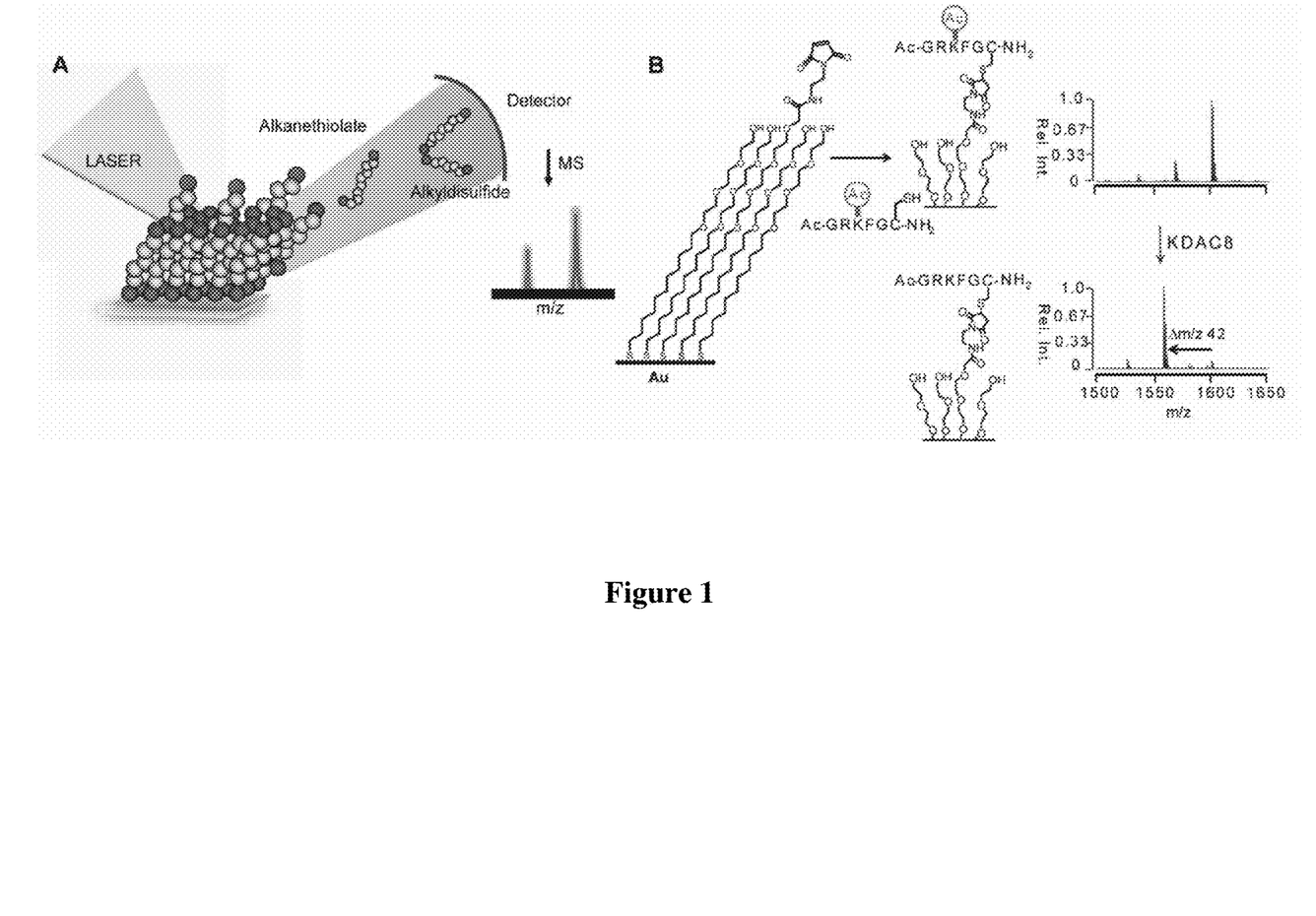
FIG. 1 depicts the SAMDI method. (A) In the SAMDI method, a laser causes desorption and ionization of alkanethiolates that are then identified in the MS spectrum. (B) Peptides are covalently immobilized to a maleimide-presenting surface. Post-translational modifications, such as deacetyalation, can be identified by characteristic mass shifts of the mass spectrum before, and after, exposure to the enzyme.

In SAMDI, the monolayer is irradiated with a laser, which results in desorption of the products and substrates through dissociation of a thiolate-gold bond, but with little fragmentation of these molecules. Hence, the resulting spectra are straightforward to interpret. FIG. 1 shows an example of an assay performed with SAMDI and shows spectra corresponding to a monolayer presenting a substrate before and after treatment with a KDAC. The spectra reveal a mass change of 42 in the substrate (modified to include an alkanethiolate so as to bind to the SAM surface) that is consistent with the deacetylation reaction. Assays using this SAMDI technique can be used on a range of enzyme activities, and are quantitative, compatible with complex lysates, and adaptable to high throughput formats (Ban et al., Nat Chem Biol 8: 769-773 (2012); Li et al., Langmuir 23: 11826-11835 (2007); Su et al., Langmuir 19: 4867-4870 (2003); Su et al., Angew Chem Int Ed Eng. 41: 4715-4718 (2002); Min et al., Angewandte Chemie 43: 5973-5977 (2004); Min et al., Anal Chem 76: 3923-3929 (2004); Yeo et al., Angew Chem Int Ed Engl 44: 5480-5483 (2005); Marin et al., Angew Chem Int Ed Engl 46: 8796-8798 (2007); Patrie et al., Anal Chem 79: 5878-5887 (2007); Ban et al., Angew Chem Int Ed Eng 47: 3396-3399 (2008); Gurard-Levin et al., Annu Rev Anal Chem (Palo Alto Calif.) 1: 767-800 (2008); Gurard-Levin et al., Biochemistry 47: 6242-6250 (2008); Mrksich, ACS Nano 2: 7-18 (2008); Tsubery et al., Langmuir 24: 5433-5438 (2008); Gurard-Levin et al., Chembiochem 10: 2159-2161 (2009); Liao et al., Chemistry 15, 12303-12309 (2009); Gurard-Levin et al., ACS Chem Biol 5: 863-873 (2010); Kim et al., Nucleic Acids Res 38: e2 (2010); Cal et al., Carbohydr Res 346: 1576-1580 (2011); Gurard-Levin et al., ACS Comb Sci 13: 347-350 (2011); Liao et al., Angew Chem Int Ed Engl 50: 706-708 (2011); Prats-Alfonso et al., Small 8: 2106-2115 (2012); Li et al., Langmuir 29: 294-298 (2013)).

Figure 2:
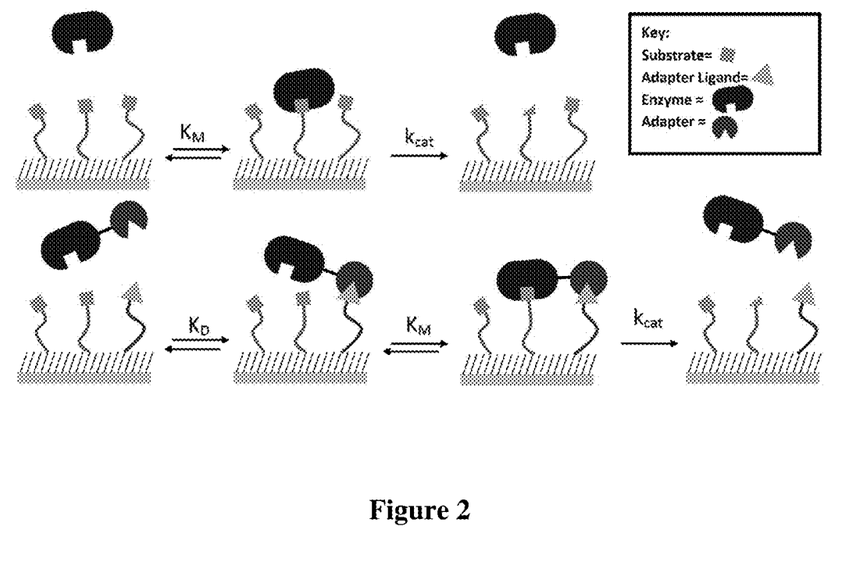
FIG. 2 shows that (Top) An enzyme can catalyze the modification of an immobilized substrate. (Bottom) When the enzyme is fused to an adaptor protein, the latter can bind to a ligand on the monolayer and recruit the enzyme to its substrate, with an acceleration in the rate for the enzyme-mediated reaction. The resulting product can be detected by SAMDI mass spectrometry and reports on the presence of the protein-ligand interaction.

Protein-ligand interaction can be used to localize an enzyme to the surface and then increase the rate of the enzyme-catalyzed reaction of an immobilized substrate by 30-fold (Li et al., J Phys Chem B 114: 15113-15118 (2010)). It has been shown that a fusion protein of an SH2 domain and cutinase (a serine esterase) can hydrolyze an ester substrate immobilized to a monolayer, and that the rate for the reaction was 30-fold greater when the monolayer also presented a peptide ligand for the SH2 domain. That is, the presence of the ligand serves to recruit the cutinase enzyme to the surface, where it then more rapidly catalyzed the hydrolysis of the ester substrate (FIG. 2). In this way, the interaction of the SH2 receptor with the peptide ligand can lead to a greater rate for the enzyme-mediated reaction of the immobilized substrate. Thus, the extent of product formation on the monolayer—which can be determined using SAMDI mass spectrometry after the assay is complete—is a measure of the protein-ligand complex. Even very weak interactions lead, with enough reaction time, to levels of enzyme-catalyzed reaction that exceed levels obtained in the absence of an interaction and therefore that can be used to characterize the receptor-ligand interaction.

In general, the disclosure provides methods in which a receptor of interest is coupled to an enzymatic activity, which acts as a reporter of a binding event. A ligand of interest and enzymatic substrate are immobilized onto chemically defined monolayers. A poor substrate is chosen, so that little conversion to product is observed when the enzyme alone is presented. When the receptor of interest is matched with a ligand, binding occurs and the enzyme is localized to the surface. When localized in close proximity to the substrate, the rate of product formation is enhanced and an increase in enzymatic activity is observed. The resulting activity is quantified directly by MALDI mass spectrometry as a shift in mass of enzyme substrate to product. Enhancement of enzymatic rate is dependent on the strength of the receptor-ligand interaction, allowing for high throughput comparison of many hundreds of binding interactions.

The methods described herein offer several advantages over existing technologies. First, the use of a monolayer substrate provides control over the immobilization and activities of ligands, including the use of surface chemistries that are otherwise inert to non-specific protein adsorption. Most surface assay work still uses blocking procedures and detergents to minimize non-specific adsorption—such procedures result in a corresponding loss in quantitative performance. Second, the present disclosure provides a class of substrates that are compatible with mass spectrometry and which radically increase the throughput of mass spectrometry. Third, the assays provided by the disclosure are label free and detection is performed by mass spectrometry, as opposed to nonspecific spectrophotometric measurements. Fourth, signal is not limited by binding strength since a history of covalent modifications is generated. Even weak interactions, which are present at low occupancy, give an accumulation of the product that can later be detected. Finally, the methods of the disclosure, which in some aspects rely on an interaction-dependent localization of enzyme and substrate, effectively translate a binding interaction into the accumulation of an enzyme-mediated product. The combination of monolayers and mass spectrometry, together with this enzyme activity localization assay provides high throughput assays of protein-ligand interactions.

Accordingly, in one aspect an immobilized substrate and an immobilized ligand are contacted with a fusion protein under conditions to transform the immobilized substrate to an immobilized product, wherein the immobilized product has a mass different from the immobilized substrate. According to the methods of the disclosure, and in some aspects, at least one of the substrate and the ligand comprises a peptide. In some embodiments, the ligand is a peptide and comprises a methylated lysine residue. In some embodiments, the peptide is bound to the SAM via a cysteine residue. In various embodiments, the enzyme is a deacetylase, acetyltransferase, esterase, phosphorylase/kinase, phosphatase, protease, methylase, demethylase, or a DNA or RNA modifying enzyme. In some embodiments, the deacetylase is KDAC8. In further embodiments, the esterase is cutinase or acetylcholine esterase. In some embodiments, the protease is TEV.

In various embodiments, the substrate comprises an acylated peptide and the product comprises a deacylated peptide. In some embodiments, the substrate comprises a deacylated peptide and the product comprises an acylated peptide. In some embodiments, the substrate comprises a phosphorylated peptide and the product comprises a dephosphorylated peptide. In various embodiments, the substrate comprises a dephosphorylated peptide and the product comprises a phosphorylated peptide. In some embodiments, the substrate comprises a methylated peptide and the product comprises a demethylated peptide. In various embodiments, the substrate comprises a demethylated peptide and the product comprises a methylated peptide.

In another aspect, the present disclosure provides a high throughput screen utilizing (i) a fusion protein comprising a receptor and an enzyme capable of transforming an immobilized substrate to a product, and (ii) an immobilized ligand which in various embodiments is based on a methylated peptide. In some aspects, the immobilized substrate for the enzyme and the immobilized ligand for the receptor are each bound to a self-assembled monolayer (SAM) on a surface, wherein the total density of the ligand and the substrate on the surface is less than or equal to about 10%. The immobilized substrate and the immobilized ligand are contacted with the fusion protein under conditions that transform the immobilized substrate to an immobilized product, wherein the immobilized product has a mass different from the immobilized substrate. The substrate and product are then subjected to mass spectrometry to produce a mass spectrum having a product signal and a substrate signal, and binding of the receptor and the ligand is detected by correlating a signal intensity of the product to a signal intensity of the substrate to determine the extent of product formation and thereby detecting the binding of the receptor and the ligand.

As used herein, the "density" of the ligand and the substrate on the surface refers to the fraction of alkanethiolates of the monolayer that are attached to the surface (e.g., a gold surface) and that are modified with the substrate and the ligand. In one embodiment, the total density of the ligand and the substrate on the surface is less than or equal to about 10%. In some embodiments, the total density of the ligand and the substrate on the surface is less than or equal to about 9%, or is less than or equal to about 8%, or is less than or equal to about 7%, or is less than or equal to about 6%, or is less than or equal to about 5%, or is less than or equal to about 4%, or is less than or equal to about 3%. In additional embodiments, the total density of the ligand and the substrate on the surface is from about 3% to about 7%, or from about 4% to about 7%, or from about 5% to about 7%, or from about 3% to about 6%, or from about 4% to about 6%, or from about 5% to about 6%. In further embodiments, the total density of the ligand and the substrate on the surface is at least 0.1%, at least 0.2%, at least 0.5%, at least 0.6%, at least 0.7%, at least 0.8%, at least 0.9%, at least 1%, at least 1.5%, at least 2%, at least 2.5%, at least 3%, at least 3.5%, at least 4%, at least 4.5%, at least 5%, at least 5.5%, at least 6%, at least 6.5%, at least 7%, at least 7.5%, at least 8%, at least 8.5%, at least 9%, or at least 9.5%.

In various embodiments, the ligand has a dissociation constant ($K_D$) of about 10 pM to about 100 μM. In further embodiments, the ligand has a dissociation constant ($K_D$) of about 100 nM to about 10 μM. In various embodiments, the $K_D$ is less than 10 μM. In some embodiments, the ligand has a $K_D$ of about 10 pM to about 50 μM, or about 30 pM to about 50 μM, or about 50 pM to about μM, or about 100 pM to about 100 μM, or about 500 pM to about 100 μM, or about 500 pM to about 50 μM, or about 1 nanomolar (nM) to about 100 μM, or about 1 nM to about 50 μM, or about 1 nM to about 40 μM, or about 1 nM to about 30 μM, or about 1 nM to about 20 μM, or about 1 nM to about 10 μM, or about 10 nM to about 100 μM, or about 10 nM to about 50 μM, or about 10 nM to about 40 μM, or about 10 nM to about 30 μM, or about 10 nM to about 20 μM, or about 10 nM to about 10 μM, or about 50 nM to about 100 μM, or about 50 nM to about 50 μM, or about 50 nM to about 40 μM, or about 50 nM to about 30 μM, or about 50 nM to about 20 μM, or about 50 nM to about 10 μM, or about 100 nM to about 100 μM, or about 100 nM to about 50 μM, or about 100 nM to about 40 μM, or about 100 nM to about 30 M, or about 100 nM to about 20 μM, or about 100 nM to about 5 μM. In some embodiments, the ligand has a $K_D$ of about 10 pM, about 20 pM, about 50 pM, about 100 pM, about 150 pM, about 300 pM, about 400 pM, about 500 pM, about 1 nM, about 5 nM, about 10 nM, about 20 nM, about 50 nM, about 75 nM, about 100 nM, about 150 nM, about 300 nM, about 400 nM, about 500 nM, about 1 μM, about 2 μM, about 3 μM, about 4 μM, about 5 μM, about 6 μM, about 7 μM, about 8 μM, about 9 μM, about 10 μM, about 11 μM, about 12 μM, about 13 μM, about 14 μM, about 15 μM, about 16 μM, about 17 μM, about 18 μM, about 19 μM, or about 20 μM.

In some embodiments, the substrate density on the surface is greater than the ligand density on the surface.

In any of the embodiments of the disclosure, the extent of product formation in the presence of the fusion protein is greater than extent of product formation in the presence of the enzyme not fused to the receptor. In further embodiments, the extent of product formation in the presence of the fusion protein is at least 2 times greater, at least 5 times greater, at least 10 times greater, at least 20 times greater, at least 30 times greater, or at least 50 times greater than extent of product formation in the presence of the enzyme not fused to the receptor.

It is further contemplated that at least one of the substrate and ligand is bound to the SAM and surface via a linker. In some cases, each of the substrate and ligand is bound to the SAM and surface via a linker. The linker, in some aspects, has a structure of formula I:

(formula I)

wherein L is the substrate or ligand.

In some embodiments, L is attached to the pyrrolindinone of formula (I) via a thiol bond. In some embodiments, the linker is attached to the SAM via an ethylene glycol moiety, and in additional embodiments the SAM is attached to the surface via a thiol bond.

Surface.

The surface can be any material capable of forming a monolayer, e.g., a monolayer of alkanethiols. Particularly, the substrate may be a metal, such as Au, Ag, Pd, Pt, Cu, Zn, Fe, In, Si, $Fe_2O_3$, $SiO_2$ or ITO (indium tin oxide) glass. In various embodiments, the disclosure contemplates that a surface useful in the methods described herein comprises Au, Ag, or Cu.

Receptors as Drug Targets.

As used herein, "receptors" are families of proteins that recognize peptide motifs and that play an essential role in all signaling processes by controlling the association of proteins in the cell. For example, SH2 domains bind peptide motifs having a phosphotyrosine residue, bromodomains bind to motifs having an acetylated lysine residue and chromodomains bind to motifs having a methylated lysine residue (Cabrera-Pardo et al., Nat Chem 5: 423-7 (2013); Sudol, Oncogene 17: 1469-1474 (1998); Sanchez et al., Curr Opin Drug Discov Devel 12: 659-665 (2009)). Receptors represent a largely novel class of targets for drug discovery, but the lack of an enzymatic activity makes these targets difficult to screen. The SH2 domains, involved in kinase signaling cascades and transcriptional regulation, have become the target of selective inhibition over the past decade (Kraskouskaya et al., Chem Soc Rev 42: 3337-3370 (2013)). The SH2 domain of the c-Src kinase, targeted for its role in oncogenesis, is one example wherein inhibitors have been developed. "Eepigenetic" targets have recently become priorities in drug development (Buchanan et al., Bioorg Med Chem Lett 9: 2353-2358 (1999); Sperl et al., Bioorg Med Chem Lett 19: 3305-3309 (2009)). These targets include the enzymes that regulate protein methylation and acetylation and include the bromo- and chromodomains that are involved in reading these modifications in the context of the nucleo some. Several programs are now developing inhibitors of the histone acetyl transferases and deacetylases for treatments in cancer and other diseases (Dekker et al., Drug Discov Today 14: 942-948 (2009); Lane et al., J Clin Oncol 27: 5459-5468 (2009)). Within the epigenetics space, recent work has emphasized the importance of the adaptor domains as targets in drug discovery. For example, an inhibitor of the BET family of bromodomain (Brd2, Brd3, and Brd4) was identified as an upregulator of the anti-inflammatory gene ApoA1 (Chung et al., J Med Chem 54: 3827-3838 (2011)). However, this inhibitor was discovered serendipitously while looking for small molecule upregulators of the gene and other attempts to design inhibitors of chromodomains based on their native methyllysine substrates have not yielded high affinity inhibitors (Herold et al., J Med Chem 54: 2504-2511 (2011); Herold et al., Curr Chem Genom 5: 51-61 (2011)). The present disclosure provides methods of conducting high throughput assays that can screen libraries to identify modulators of protein-ligand interactions which enable drug discovery on this exciting set of targets.

Receptors contemplated by the present disclosure include, without limitation, a chromodomain, a bromodomain, a PDZ domain, a Src homology 2 (SH2) domain SH2 domain, or a PDZ domain. In some embodiments, the chromodomain is a HP1 chromodomain, or a Pc chromodomain.

Chromodomains.

Chromodomains bind to peptides having methylated lysine residues. These domains have not yet been extensively characterized but have already emerged as high interest targets for drug discovery even though there is currently a lack of assays suitable for screening. In that sense, the chromodomains are a strategic target for the proposed work and offer a strong potential to enable discovery of novel drug leads in cancer. The chromodomains can be subdivided into three families of proteins that mediate recognition of histone proteins in the nucleosome and play an essential role in the epigenetic control of a broad array of cellular processes (Eissenberg, Gene 496: 69-78 (2012)). They contribute to the gene silencing that is associated with histone methylation. In some embodiments, the present disclosure contemplates the use of (i) two Pc chromodomains, which are members of the polycomb group proteins and are involved in regulation of developmental genes and (ii) three chromodomains from the HP1 proteins which are localized at chromosomal sites that are highly condensed and unexpressed (Fanti, Curr Opin Genet Dev 18: 169-174 (2008)). These proteins are known to bind at histone H3 lysine 9 (H3K9) as well as the H3K27 site, with HP1 chromodomains favoring the H3K9 position and Pc chromodomains favoring the H3K27 position. Early work reported that the interactions are relatively weak, with dissociation constants of about 1-10 µM for good binding partners and greater than 100 µM for non-ideal binding partners (Fanti, Curr Opin Genet Dev 18: 169-174 (2009); Hublitz et al., Int J Dev Biol 53: 335-354 (2009); Dormann et al., Cell Cycle 5: 2842-2851 (2006); Bannister et al., Nature 410: 120-124 (2001); Whitcomb et al., Trends Genet 23: 494-502 (2007)).

Screening for Protein-Protein Interactions.

A variety of approaches are now used to measure protein interactions, including those based on surface plasmon resonance spectroscopy, isothermal calorimetry, FRET, fluorescence polarization, and protein complementation (Garske et al., Nat Chem Biol 6: 283-290 (2010); Liu et al., J Proteome Res 9: 5827-5836 (2010); Eisert et al., ChemBioChem 12: 2786-2790 (2011); Volkmer et al., FEBS Lett 586: 2780-2786 (2012); Kaustov et al., J Biol Chem 286: 521-529 (2011)). These methods, however, are not well-suited to high throughput screening, either because they have a limited throughput or they lack generality and require a substantial effort to develop the labeled proteins required in a particular assay. The development of peptide arrays—primarily the SPOT method (commercial phase peptide synthesis method that utilizes cellulose sheets as the solid support)—offers dramatically increased throughputs in assays of protein binding. This method prepares arrays through the solid phase synthesis of peptides on a nitrocellulose substrate and uses labeled proteins to measure the extent of binding to the immobilized peptides (Volkmer et al., FEBS Lett 586: 2780-2786 (2012); Kaustov et al., J Biol Chem 286: 521-529 (2011)). However, the assays are largely qualitative, still dependent on labels and particularly ill-suited to the observation of low affinity protein interactions, since the detection is not performed in real time. The present disclosure combines self-assembled monolayers as substrates that provide quantitative assays with mass spectrometry to detect an enzyme activity associated with a protein-ligand complex and also provide a reliable and high throughput technology for applications in early stage drug discovery.

Accordingly, in some aspects of the disclosure, at least one of the substrate or the ligand is a protein. Proteins are understood in the art and include without limitation an antibody, an enzyme, a structural polypeptide and a hormone. Regardless of the protein of interest, the methods of the disclosure are amenable to measuring protein-protein binding interactions.

As used herein a "protein" refers to a polymer comprised of amino acid residues and may also be referred to as a "polypeptide" in the art. Consistent with the understanding in the art, "protein" can also refer to the association (covalent or non-covalent) of distinct "polypeptide" or "protein" polymers or chains.

"Amino acids" are organic compounds that combine to form proteins. Amino acids are typically classified as either essential, nonessential, and conditional. Essential amino acids cannot be made by the reference body, typically a human body. As a result, they must come from food. The nine essential amino acids for humans are: histidine, isoleucine, leucine, lysine, methionine, phenylalanine, threonine, tryptophan, and valine. "Nonessential" means that the body, such as the human body, produces an amino acid, even if it is not obtained from the food we eat. Nonessential amino acids include alanine, asparagine, aspartic acid, and glutamic acid. Conditional amino acids are usually not essential, except in times of illness and stress; for humans, these include arginine, cysteine, glutamine, tyrosine, glycine, ornithine, proline, and serine.

Proteins of the present disclosure may be either naturally occurring or non-naturally occurring.

Naturally occurring proteins include, without limitation, biologically active proteins (including antibodies) that exist in nature or can be produced in a form that is found in nature by, for example, chemical synthesis or recombinant expression techniques. Naturally occurring proteins also include lipoproteins and post-translationally modified proteins, such as, for example and without limitation, glycosylated proteins.

Antibodies contemplated for use in the methods and compositions of the present disclosure include without limitation antibodies that recognize and associate with a target molecule either in vivo or in vitro.

Structural polypeptides contemplated by the disclosure include without limitation actin, tubulin, collagen, elastin, myosin, kinesin and dynein.

Non-naturally occurring proteins contemplated by the present disclosure include but are not limited to synthetic proteins, as well as fragments, analogs and variants of naturally occurring or non-naturally occurring proteins as defined herein. Non-naturally occurring proteins also include proteins or protein substances that have D-amino acids, modified, derivatized, or non-naturally occurring amino acids in the D- or L-configuration and/or peptidomimetic units as part of their structure.

Non-naturally occurring proteins are prepared, for example, using an automated polypeptide synthesizer or, alternatively, using recombinant expression techniques using a modified polynucleotide that encodes the desired protein.

As used herein a "fragment" of a protein is meant to refer to any portion of a protein smaller than the full-length protein expression product.

As used herein an "analog" refers to any of two or more proteins substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physicochemical or functional relatedness of the amino acid that is being replaced and the amino acid replacing it.

As used herein a "variant" refers to a protein or analog thereof that is modified to comprise additional chemical moieties not normally a part of the molecule. Such moieties may modulate, for example and without limitation, the molecule's solubility, absorption, and/or biological half-life. Moieties capable of mediating such effects are disclosed in Remington's Pharmaceutical Sciences (1980). Procedures for coupling such moieties to a molecule are well known in the art. In various aspects, polypeptides are modified by glycosylation, PEGylation, and/or polysialylation.

Fusion proteins, including fusion proteins wherein one fusion component is a fragment or a mimetic, are also contemplated. A "mimetic" as used herein means a peptide or protein having a biological activity that is comparable to the protein of which it is a mimetic. By way of example, an endothelial growth factor mimetic is a peptide or protein that has a biological activity comparable to the native endothelial growth factor. The term further includes peptides or proteins that indirectly mimic the activity of a protein of interest, such as by potentiating the effects of the natural ligand of the protein of interest. A "peptide," as is understood in the art and as used herein, is generally shorter (i.e., comprises fewer amino acids) than a protein.

KDAC as a Reporter Enzyme.

In some embodiments of the disclosure, the lysine deacetylase KDAC8 is utilized as a reporter enzyme. This enzyme can deacetylate appropriate peptide substrates on a monolayer and it has been shown that the assay works well in cell lysate. Further, a high throughput screen of inhibitors has been performed for this enzyme and the screen was shown to be of high quality (the Z'-factor was 0.84) (Gurard-Levin et al., Biochemistry 47: 6242-6250 (2008); Gurard-Levin et al., Chembiochem 10: 2159-2161 (2009); Gurard-Levin et al., ACS Chem Biol 5: 863-873 (2010); Gurard-Levin et al., ACS Comb Sci 13: 347-350 (2011); Mwakwari et al., J Med Chem 53: 6100-6111 (2010); Patil et al., J Med Chem 56: 3492-3506 (2013)).

High Throughput Formats for SAMDI.

An improvement to the SAMDI method is disclosed herein. The improved method translates SAMDI to a high throughput format based on standard 384 and 1536 microtiter plate formats. This format uses a stainless steel plate in the size of a microtiter plate and having an array of gold-coated islands modified with a monolayer presenting maleimide groups (e.g., linkers of formula I) against a background of tri(ethylene glycol) groups. Peptides are then immobilized to each of the islands; in a high throughput screen each island has the same peptide whereas in an experiment to identify active substrates for an enzyme each spot would present a different peptide. Standard robotic liquid handling equipment can be used to prepare arrays of reactions and to transfer those reaction mixtures to the array plates. The treated plates are incubated (e.g., between 30-60 minutes), washed, and a solution of matrix is applied to the surface. The plate is then loaded into a MALDI-ToF instrument, and each spot is analyzed in an automated fashion in approximately 30 minutes. Resulting data is analyzed using custom written software that can compare the location and magnitude of the peaks in the SAMDI spectra to a reference mass file unique to each set of peptides to look for specific reaction profiles based on characteristic mass shifts (i.e., −42 for deacetylation, +80 for phosphorylation, +14 for methylation). The software presents the data in a manner that can be further analyzed with standard commercial packages (such as Excel) to identify hits in a high throughput screen, or to generate heatmaps of activities. Recent work has demonstrated the screening of 100,000 molecules against the KDAC8 deacetylase (Gurard-Levin et al., ACS Comb Sci 13: 347-350 (2011)).

Modulators/Activators.

As described herein, one aspect the disclosure provides a method comprising contacting an immobilized substrate and an immobilized ligand with a fusion protein under conditions to transform the immobilized substrate to an immobilized product, wherein the immobilized product has a mass different from the immobilized substrate. In some embodiments, the immobilized substrate and the immobilized ligand are contacted with the fusion protein in the presence of one or more potential modulators of the receptor-ligand binding; subjecting the substrate and product to mass spectrometry to produce a mass spectrum having a product signal and a substrate signal; and binding of the receptor and the ligand is detected by correlating a signal intensity of the product to a signal intensity of the substrate to determine the extent of product formation and thereby detecting the binding of the receptor and the ligand in the presence of the one or more potential modulators.

In some embodiments, the modulator is an inhibitor of the receptor-ligand binding. In further embodiments, the modulator is an activator of the receptor-ligand binding.

In any of the embodiments of the disclosure, the method further comprises admixing a matrix to the substrate and product prior to subjecting the substrate and product to mass spectrometry.

EXAMPLES

Example 1

Design and Construction of a Method to Monitor and Measure Weak Interactions

In this example, two peptides—a methylated peptide that binds the chromodomain and an acetylated peptide that is a substrate for the deacetylase—are immobilized to a monolayer presenting maleimide groups against a background of tri(ethylene glycol) groups. The density of the maleimide group is controlled precisely (Houseman et al., Langmuir 19: 1522-1531 (2003)) and the relative densities of the two peptides are controlled either by immobilizing them as a mixture at defined concentrations or by immobilizing the first for a time that gives incomplete immobilization followed by addition of the second peptide. Fusion proteins are prepared by first constructing E. coli-based vectors containing chromodomains and KDAC8 separated by a short linker. The vector is designed to contain a restriction site allowing for the insertion of any chromodomain of interest containing the complementary restriction sites. In this way, the same plasmid containing KDAC8 may be used to rapidly create several chromodomain fusions. Monolayers are treated with the chromodomain-KDAC8 fusion protein for different times, the reactions are stopped by rinsing and the spots are analyzed by SAMDI mass spectrometry to identify an initial velocity for the reaction, $v_o$, which is the measurable parameter that is used to assess the protein-ligand interaction.

Design and Synthesis of Peptide Ligands.

The Pc and HP1 chromodomains are used, which have been shown to bind histones methylated at residues H3K27 and H3K9. Peptide ligands are used that are based on the sequences immediately surrounding these sites: QTARK$_9$STGG (SEQ ID NO: 1) and KAARK$_{27}$SAPS (SEQ ID NO:2). The goal is to identify several ligands for each chromodomain, such that the ligands have dissociation constants that vary from 1 to 50 μM.

Potential additional experiments involve evaluating peptides having phosphorylation at T6, S10, S28, and S31; methylation of R8 and K23; acetylation of K23; and citrullination of R8, all of which are known and are tested for their effects on affinity. The peptides based on the sequences of these sites are synthesized using standard solid phase peptide synthesis and FMOC chemistry in order to probe the affinity of different chromodomains for these sites and their post translationally modified forms. Surface plasmon resonance spectroscopy is used to independently measure the binding affinities of the chromodomains for the immobilized peptides, as has been performed previously (Houseman et al., Angew Chem Int Ed 38: 782-785 (1999); Luk et al., Langmuir 16: 9604-9608 (2000); Mrksich, Chem Soc Rev 29: 267-273 (2000); Houseman et al., Chem Biol 9: 443-454 (2002); Sigal et al., Langmuir 13: 2749-2755 (1997); Hodneland et al., J Am Chem Soc 122, 4235-4236 (2000)).

Optimization of Assay.

Figure 3:
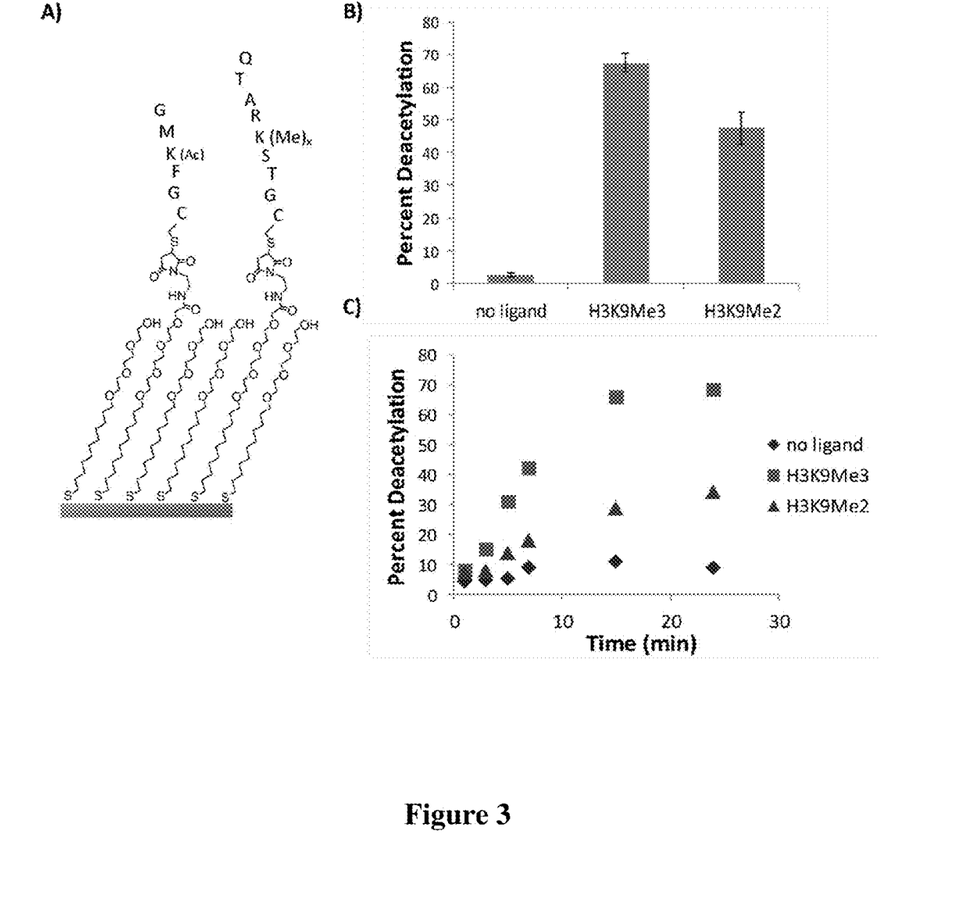
FIG. 3 shows that (A) A poor KDAC8 substrate can be co-immobilized onto a surface with binding peptides for the Cbx1 chromodomain from the HP1 family. (B) After 25 minutes at room temperature, a dramatic increase in activity is observed for the monolayers presenting a ligand for the chromodomain. (C) The extents of reaction are determined using SAMDI.

The Cbx1 fusion protein was prepared and applied to monolayers presenting the peptides GMK$^{Ac}$FGC (SEQ ID NO: 3) and QTARK$^{Me}$STGC (SEQ ID NO: 4). The results showed a rate acceleration for the deacetylation reaction of approximately 20-fold when the chromodomain binds its ligand on the monolayer. Increased activity was observed on surfaces presenting both di- and tri-methylated peptides corresponding to H3K9 (FIG. 3). Both single time point experiments(b) and kinetic profiles (c) showed that the observed activity increased with the methylation state. Importantly, this example establishes that the model system is well-suited to the proposed work.

The direct output of the assay is the initial velocity for the deacetylation reaction and it represents a weighted average of the rates for the background reaction (where the chromodomain is not bound to its ligand) and the accelerated reaction observed when the chromodomain is bound to the monolayer. An ideal rate law is shown below, where E is the total enzyme concentration, Γ is a concentration term that represents the density of the initial substrate ($S_o$), the deacetylated product (P) and the bound chromodomain-peptide complex (C). Note that the difference in density between total peptide substrate and deacetylated product ($\Gamma_{So}$-$\Gamma_P$) represents the density of substrate at any time in the reaction: Rate=$[E]k_b(\Gamma_{So}$-$\Gamma_P)+\Gamma_c k_t(\Gamma_{So}$-$\Gamma_P)$.

These experiments demonstrate the assay and validate that there is a quantitative relationship between $\upsilon_o$ and the binding affinity of the chromodomain-peptide complex. As described above, monolayers presenting one of a series of peptide ligands for the chromodomain are prepared together with the substrate for KDAC8 and the initial rates of deacetylation at several concentrations of the fusion protein are measured. In this assay, the deacetylation reaction is unchanged—that is, both the enzyme and substrate remain the same as the ligand for the chromodomain is varied. Any change in observed activity is attributed to the strength of the adapter domain-ligand interaction. The rate is dependent on the amount of protein-ligand complex formed ($\Gamma_c$), and change in the strength of the interaction (in the $K_D$) therefore corresponds to the measurable change in initial velocity. This allows for quantitative comparison of $K_D$ for different ligands using SAMDI. As stated earlier, surface plasmon resonance (on a Biacore instrument, using monolayer substrates that are prepared, as described in the art) is used to directly measure the dissociation constants for the complexes as well as the rate constants for association and dissociation. In this way, the SAMDI assay is used to measure values of $\upsilon_o$ in order to determine whether this value is linearly related to the binding affinity of the complex. It is also recognized that the $\upsilon_o$ value may be influenced by kinetic terms for association and dissociation of the protein (since a bound protein will also 'mask' some of the available KDAC substrates on the monolayer) and therefore a panel of peptides will be used that have a range of $k_a$ and $k_d$ values to see if these terms impact the $\upsilon_o$ measured in the assay. Experiments are also performed in which the relative densities of the binding ligand and the enzyme substrate are varied in order to determine the sensitivity of the assay to changes in these densities. This information is important to optimizing the sensitivity of the assay and the reproducibility of monolayers that are used in the assay. For example, a high throughput screen will use 100 array plates and a high sensitivity to small changes in density of the ligand could dramatically decrease Z'-factors. Finally, plate uniformity studies and plate-to-plate uniformity are performed to understand the intrinsic noise in the assay. This information will allows for the optimization of the reagents and assay conditions to perform high throughput screens.

Example 2

Screening for Protein Binding Inhibition

This example describes a screen of the chromodomain Cbx1 binding to the ligand H3K9(Me)$_3$. The screen uses a commercial library of 130,000 compounds. This example will determine the Z-factor for the screen and has the dual goal of validating the approach for screening low affinity ligand-receptor interactions and also in identifying first generation compounds that can inhibit the chromodomain.

These experiments apply the assay discussed in Example 1 to a high throughput screen of 130,000 small molecules to identify inhibitors of the chromodomains. One paper to date has disclosed inhibitors of chromodomains and those inhibitors are based on methyllysine analogues (Herold et al., J Med Chem 54: 2504-2511 (2011)). A related report recently disclosed an inhibitor of a bromodomain that may have anti-inflammatory properties (Chung et al., J Med Chem 54, 3827-3838 (2011)).

High-Throughput Inhibitor Screening.

Figure 4:
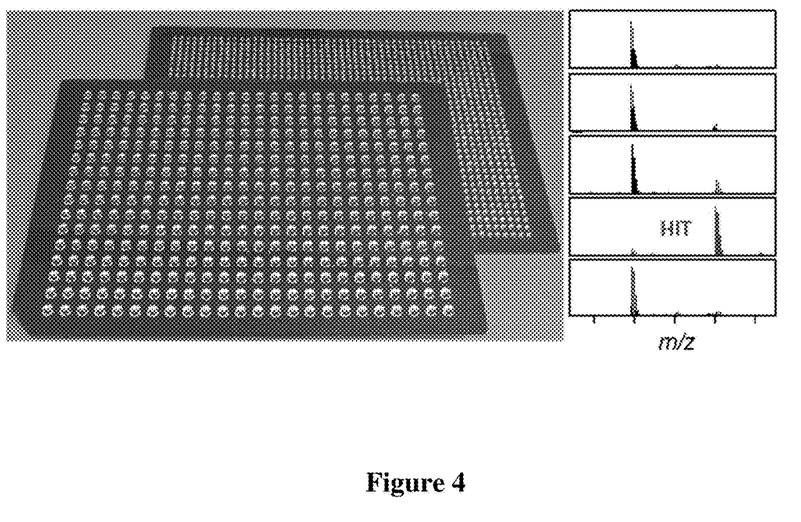
FIG. 4 depicts (Left Side) 384 and 1536 position arrays spotted with enzymatic cocktails containing potential small molecule inhibitors. (Right side) SAMDI spectra showing no inhibition (spectra 1, 2, 3, and 5) or high inhibition (fourth spectra from top).

The screen is performed with the workflow used in a recent report of a screen of KDAC8 (Gurard-Levin et al., ACS Comb Sci 13: 347-350 (2011)). Due to the nature of the protein-binding assay, this work requires that the reactions be performed on the monolayer, and not in a homogenous solution format as in the previous work. Array plates having 1,536 gold islands are prepared in the standard geometry and each modified with a monolayer that presents defined densities of the substrate and ligand—for example, 2% of the chromodomain substrate and 8% of the KDAC8 substrate covalently immobilized to a SAM on gold islands. Liquid handling robots are used to prepare 1536 well plates that contain the enzyme, a pool of eight molecules from the 130,000 small molecule library (from the Chembridge Diverset), and buffer. These reaction mixtures are transferred to the monolayer array plate, incubated for 30 minutes, and then rinsed to terminate reactions. The monolayers are treated with matrix and analyzed by SAMDI mass spectrometry. The compatibility of SAMDI with the 384 and 1536 microtiter standards (see the plates in FIG. 4) allows for many thousands of individual assays to be performed in a matter of hours. The Z'-factor for the screen is determined first by evaluating the positive and negative controls across the 1536 well plate when treated with enzyme. For the negative control, half of the plate will use monolayers that present the KDAC substrate but not the ligand for the chromodomain. For the positive control, the other half of the plate will be treated with both the KDAC substrate and chromodomain ligand. The mean and standard deviation are determined for the positive and negative controls to calculate the Z'-factor. Protein-binding assays with Z'-factors greater than 0.5 are suitable for screening. The SAMDI assay has Z'-factor values of 0.85 for enzyme activities, and a value of 0.7 is targeted for protein binding assays as described herein.

Confirmation Assays.

For those wells that give more than 30% inhibition of the deacetylase activity, the compound pools are deconvoluted by assaying each of the eight compounds individually. For those that are active, the concentration-dependence on inhibition is determined to measure an $IC_{50}$ value. These inhibitors are also characterized using surface plasmon resonance spectroscopy to measure the dissociation constants. In this way, it is confirmed that the hits in the screen are not false positives and it is also confirmed that the $IC_{50}$ values measured using the assay give a quantitative measure of the compound potencies.

What is claimed is:

1. A method comprising
   (a) contacting an immobilized substrate and an immobilized ligand with a fusion protein under conditions to transform the immobilized substrate to an immobilized product, wherein
   the immobilized product has a mass different from the immobilized substrate;
   the fusion protein comprises (1) an enzyme capable of transforming the substrate to the product and (2) a receptor, and
   the immobilized substrate for the enzyme and the immobilized ligand for the receptor are each separately bound to a self-assembled monolayer (SAM) on a surface, and wherein the contacting is in the presence of one or more potential modulators of binding of the receptor and the ligand;
   (b) subjecting the substrate and product to mass spectrometry to produce a mass spectrum having a product signal and a substrate signal; and
   (c) detecting binding of the receptor and the ligand by correlating a signal intensity of the product to a signal intensity of the substrate to determine the extent of product formation and thereby detecting the binding of the receptor and the ligand in the presence of the one or more potential modulators,
   wherein the total density of the ligand and the substrate on the surface is less than or equal to about 10%, and wherein the ligand has a dissaciation constant ($K_d$) of about 10 pM to about 100 μM..

2. The method of claim 1, wherein the total density of the ligand and the substrate on the surface is from about 3% to about 7% or from about 5% to about 6%.

3. The method of claim 1, wherein extent of product formation in the presence of the fusion protein is greater than extent of product formation in the presence of the enzyme not fused to the receptor.

4. The method of claim 1, wherein at least one of the substrate and ligand is bound to the surface via a linker.

5. The method of claim 4, wherein the linker has a structure of formula I:

(formula I)

wherein L is the substrate or ligand.

6. The method of claim 5, wherein L is attached to the pyrrolidinone of formula (I) via a thiol bond.

7. The method of claim 4, wherein the linker is attached to the SAM via an ethylene glycol moiety.

8. The method of claim 1, wherein the SAM is attached to the surface via a thiol bond.

9. The method of claim 1, wherein the surface comprises gold, silver, or copper.

10. The method of claim 1, wherein at least one of the substrate and the ligand comprises a peptide.

11. The method of claim 10, wherein the peptide is bound to the SAM via a cysteine residue.

12. The method of claim 1, wherein the enzyme is a deacetylase, acetyltransferase, esterase, phosphorylase/kinase, phosphatase, protease, methylase, demethylase, or a DNA or RNA modifying enzyme.

13. The method of claim 12, wherein the substrate comprises an acylated peptide and the product comprises a deacylated peptide, the substrate comprises a phosphorylated peptide and the product comprises a dephosphorylated peptide, or the substrate comprises a methylated peptide and the product comprises a demethylated peptide.

14. The method of claim 1, wherein the receptor is a chromodomain, a bromodomain, a PDZ domain, a Src homology 2 (SH2) domain SH2 domain, or a PDZ domain.

15. The method of claim 1, wherein the ligand is a peptide and comprises a methylated lysine residue.

16. The method of claim 1, wherein the substrate density on the surface is greater than the ligand density on the surface.

17. The method of claim 1, wherein the ligand has a dissociation constant ($K_D$) of about 100 nM to about 10 μM, or less than 10 μm.

18. The method of claim 1, wherein the modulator is an inhibitor of the receptor-ligand binding.

19. The method of claim 1, further comprising admixing a matrix to the substrate and product prior to subjecting the substrate and product to mass spectrometry.

20. The method of claim 1, wherein the total density of the ligand and the substrate on the surface is from about 4% to about 7%.

21. The method of claim 1, wherein the total density of the ligand and the substrate on the surface is from about 3% to about 6%.

22. The method of claim 1, wherein the modulator is an activator of the receptor-ligand binding.

23. The method of claim 1, wherein the ligand has a dissociation constant (Ko) of about 100 nM to about 100 pM.

* * * * *

SEQUENCE LISTING

```
<160> NUMBER OF SEQ ID NOS: 4

<210> SEQ ID NO 1
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1

Gln Thr Ala Arg Lys Lys Lys Lys Lys Lys Lys Lys Ser Thr Gly
1               5                   10                  15

Gly

<210> SEQ ID NO 2
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 2

Lys Ala Ala Arg Lys Lys Lys Lys Lys Lys Lys Lys Lys Lys Lys
1               5                   10                  15

Lys Lys Lys Lys Lys Lys Lys Lys Lys Lys Lys Lys Lys Lys Ser
            20                  25                  30

Ala Pro Ser
        35

<210> SEQ ID NO 3
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Acetylation

<400> SEQUENCE: 3

Gly Met Lys Phe Gly Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (5)..(5)
```

```
<223> OTHER INFORMATION: Methylation

<400> SEQUENCE: 4

Gln Thr Ala Arg Lys Ser Thr Gly Cys
1               5
```